(12) United States Patent
Montano et al.

(10) Patent No.: US 7,179,344 B1
(45) Date of Patent: Feb. 20, 2007

(54) METHOD AND APPARATUS FOR TESTING THE QUALITY OF CRIMPED SEALS

(75) Inventors: Louis M. Montano, Oak Harbor, OH (US); Justin M. Montano, Oak Harbor, OH (US); William J. Witzler, Bowling Green, OH (US)

(73) Assignee: Lako Tool & Manufacturing, Inc., Perrysburg, OH (US)

( * ) Notice: Subject to any disclaimer, the term of this patent is extended or adjusted under 35 U.S.C. 154(b) by 0 days.

(21) Appl. No.: 10/409,621

(22) Filed: Apr. 8, 2003

Related U.S. Application Data (60) Provisional application No. 60/370,815, filed on Apr. 8, 2002.

(51) Int. Cl.
*B32B 37/10* (2006.01)
*B32B 38/10* (2006.01)
*G01N 19/04* (2006.01)

(52) U.S. Cl. .................. 156/247; 156/344; 156/358; 156/581; 156/584; 73/150 A (58) Field of Classification Search .............. 156/344, 156/584, 358, 581, 247; 29/426.5, 239; 73/150 A
See application file for complete search history.

(56) References Cited

U.S. PATENT DOCUMENTS

| | | | | |
|---|---|---|---|---|
| 2,473,517 A | * | 6/1949 | Freedman | 73/150 A |
| T916,005 I4 | * | 11/1973 | Dolen et al. | 73/150 A |
| 3,925,139 A | * | 12/1975 | Simmons | 156/358 |
| 4,795,413 A | * | 1/1989 | Johnson et al. | 493/309 |
| 5,205,650 A | * | 4/1993 | Rasmussen | 383/107 |
| 5,439,539 A | * | 8/1995 | McLean | 156/64 |
| 5,692,606 A | * | 12/1997 | Elmaleh | 206/278 |
| 5,868,901 A | * | 2/1999 | Smith | 156/582 |
| 5,972,396 A | * | 10/1999 | Jurgovan et al. | 426/106 |
| 6,230,781 B1 | * | 5/2001 | Smith | 156/582 |
| 6,478,264 B1 | * | 11/2002 | Nelson et al. | 248/65 |
| 6,609,055 B2 | * | 8/2003 | Stanley | 701/45 |

* cited by examiner

*Primary Examiner*—Mark A. Osele
(74) *Attorney, Agent, or Firm*—MacMillan, Sobanski & Todd, LLC (57) ABSTRACT

Crimped seals that are formed in overlapping portions of a packaging material are tested for quality. Initially, the packaging material is installed on first and second clamps. A portion of the packaging material is then extended between first and second crimpers. The first and second crimpers are moved into engagement with the portion of the packaging material to form a crimped seal. During this engagement, the amount of force that is exerted on the portion of the packaging material by the first and second crimpers to form the crimped seal is measured. Then, the first and second clamps are moved to pull apart the crimped seal. The amount of force that is exerted by the first and second clamps to pull apart the crimped seal is also measured. An apparatus for testing the quality of such crimped seals is also provided.

12 Claims, 8 Drawing Sheets

METHOD AND APPARATUS FOR TESTING THE QUALITY OF CRIMPED SEALS

CROSS REFERENCE TO RELATED APPLICATION

This application claims the benefit of U.S. Provisional Application No. 60/370,815, filed Apr. 8, 2002, the disclosure of which is incorporated herein by reference.

BACKGROUND OF THE INVENTION

This invention relates in general to form, fill, and seal packaging machinery of the type in which a continuous sheet of a packaging material is sequentially folded about a series of articles to be packaged, hot or cold sealed about the articles, and cut into individually sealed packages. More specifically, this invention pertains to a method and apparatus for testing the quality of crimped seals that are formed in overlapping portions of the sheet of the packaging material.

The formation of a plurality of individually sealed packages of articles using a single continuous sheet of a packaging material is well known in the art. A typical form, fill, and seal apparatus for accomplishing this is disclosed in U.S. Pat. Nos. 5,868,901 and 6,230,781, the disclosures of which are incorporated herein by reference. Briefly, however, a typical form, fill, and seal apparatus includes means for supporting a roll of a sheet of a packaging material, which is payed out and fed around various feed rollers to a folding shoe. The folding shoe continuously folds the longitudinal edges of the sheet of the packaging material about the sides of a plurality of articles which are moved longitudinally along a conveyor. The folded sheet of the packaging material is then moved along a support surface. As the folded longitudinal edges of the sheet are moved along the support surface, they are engaged by a pair of folding rollers disposed beneath the support surface. As a result, the longitudinal edges of the sheet of the packaging material are further folded downwardly in an overlapping manner. Then, a pair of grooved heat seal rollers disposed beneath the support surface engages the overlapping edges of the sheet of the packaging material so as to create a continuous longitudinal fin seal. The fin seal is next engaged by a pair of pull rollers, also disposed beneath the support surface, which advance the folded sheet of the packaging material (and the articles enclosed therein) through the apparatus. A deflector is provided in the support surface to fold the fin seal upwardly into flush engagement with the folded sheet of the packaging material.

A rotary crimping assembly is provided in the apparatus for laterally crimping and cutting the folded sheet of the packaging material so as to form a plurality of individually sealed packages. The crimping assembly includes an upper crimper bar that is disposed above the support surface for rotation about an axis extending generally perpendicular to the longitudinal movement of the sheet of the packaging material. A pair of upper crimpers are secured to opposite sides of the upper crimper bar for rotation therewith. Similarly, the crimping assembly includes a lower crimper bar that is disposed below the support surface for rotation about an axis extending generally perpendicular to the longitudinal movement of the sheet of the packaging material. A pair of lower crimpers are secured to opposite sides of the lower crimper bar for rotation therewith.

As the folded sheet of the packaging material is moved along the support surface, the upper and lower crimpers are rotated. As a result, leading edges of the upper and lower crimpers initially engage the folded sheet of the packaging material. When this occurs, the folded sheet of the packaging material is compressed between a downwardly facing crimping surface of the upper crimper and an upwardly facing crimping surface of the lower crimper. As a result, the overlapping layers that make up the folded sheet of the packaging material are sealed together to form a trailing edge seal for a packaged article. Further movement of the folded sheet of the packaging material and rotation of the upper and lower crimpers cause a cutting blade provided in one of the crimpers to be aligned with an anvil provided in the other of the crimpers. Consequently, the folded sheet of the packaging material is cut longitudinally into two pieces. Still further movement of the folded sheet of the packaging material and rotation of the upper and lower crimpers causes trailing edges of the upper and lower crimpers to engage the folded sheet of the packaging material. When this occurs, the folded sheet of the packaging material is compressed between a downwardly facing crimping surface of the upper crimper and an upwardly facing crimping surface of the lower crimper. As a result, the overlapping layers that make up the folded sheet of the packaging material are sealed together to form a leading edge seal for the next packaged article.

In some instances, the sheet of the packaging material is provided with a cohesive coating for accomplishing the seal when compressed. In other instances, an intermediate seal layer of a coating or other bonding material is provided. Also, it is sometimes desirable to heat the overlapping layers of the sheet of the packaging material when crimped to facilitate the sealing thereof. This can accomplished by heating the crimpers to an elevated temperature before compressing the layers of the packaging material therebetween.

As with most manufacturing processes, it is desirable to evaluate the quality of the crimping process in order to insure that the various overlapping layers of the packaging material will be reliably sealed when the above-described form, fill, and seal packaging machinery is operated. However, in the past, evaluations of this sort were made by operating the form, fill, and seal packaging machinery in the normal manner and removing some of the packaged articles for testing. This evaluation procedure is inefficient because the entire form, fill, and seal packaging machinery must be operated, and a number of packaged articles may have to be discarded if the seals are found to be not reliable. Thus, it would be desirable to provide a method and apparatus for testing the quality of crimped seals that are formed in overlapping portions of the sheet of the packaging material.

SUMMARY OF THE INVENTION

This invention relates to an apparatus for testing the quality of crimped seals that are formed in overlapping portions of the sheet of the packaging material. Initially, the packaging material is installed on first and second clamps. A portion of the packaging material is then extended between first and second crimpers. The first and second crimpers are moved into engagement with the portion of the packaging material to form a crimped seal. During this engagement, the amount of force that is exerted on the portion of the packaging material by the first and second crimpers to form the crimped seal is measured. Then, the first and second clamps are moved to pull apart the crimped seal. The amount of force that is exerted by the first and second clamps to pull apart the crimped seal is also measured. An apparatus for testing the quality of such crimped seals is also provided.

Various objects and advantages of this invention will become apparent to those skilled in the art from the following detailed description of the preferred embodiment, when read in light of the accompanying drawings.

DETAILED DESCRIPTION OF THE PREFERRED EMBODIMENT

Figure 1:
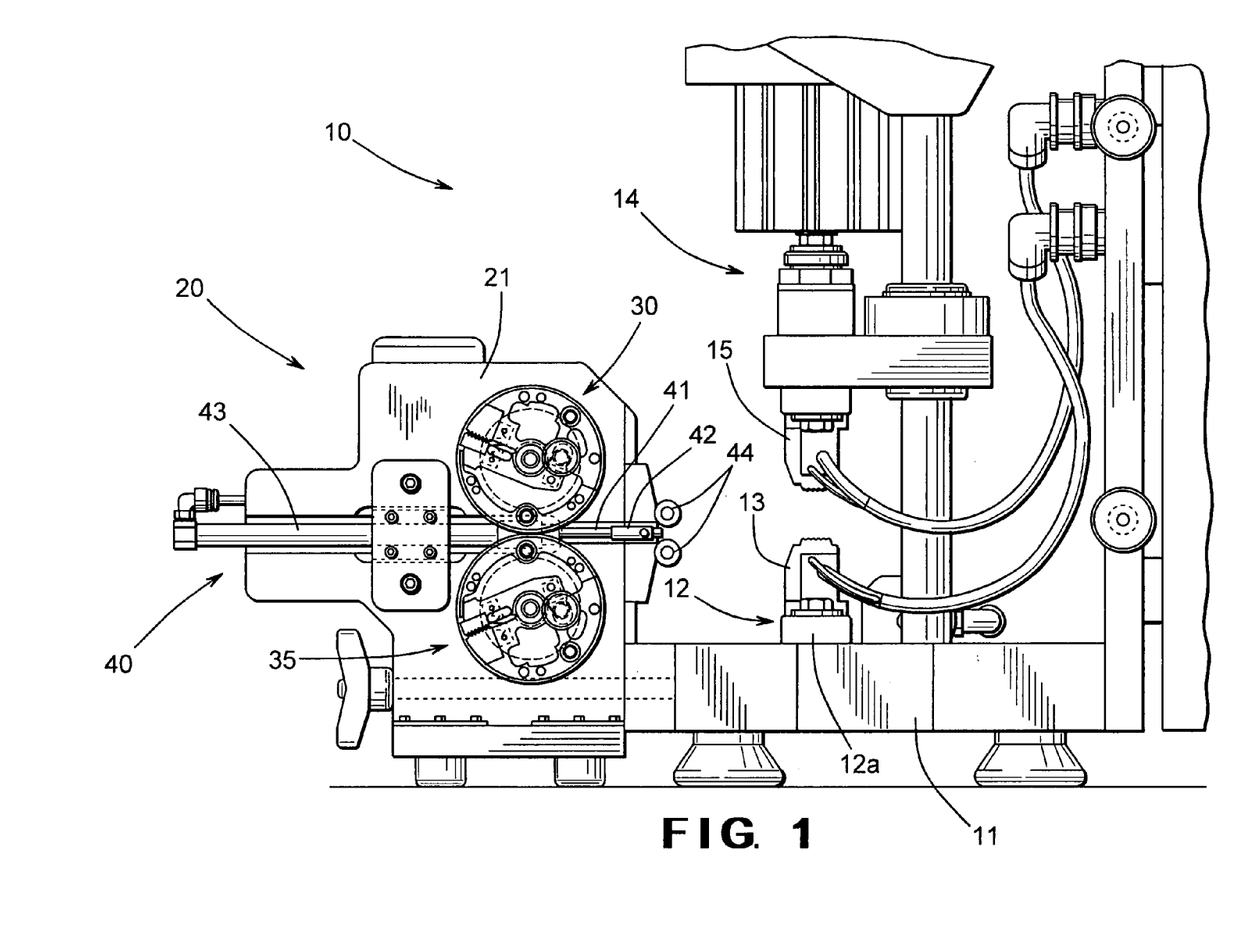
FIG. 1 is a side elevational view of a portion of an apparatus in accordance with this invention for testing the quality of crimped seals that are formed in overlapping portions of a sheet of the packaging material.
Figure 2:
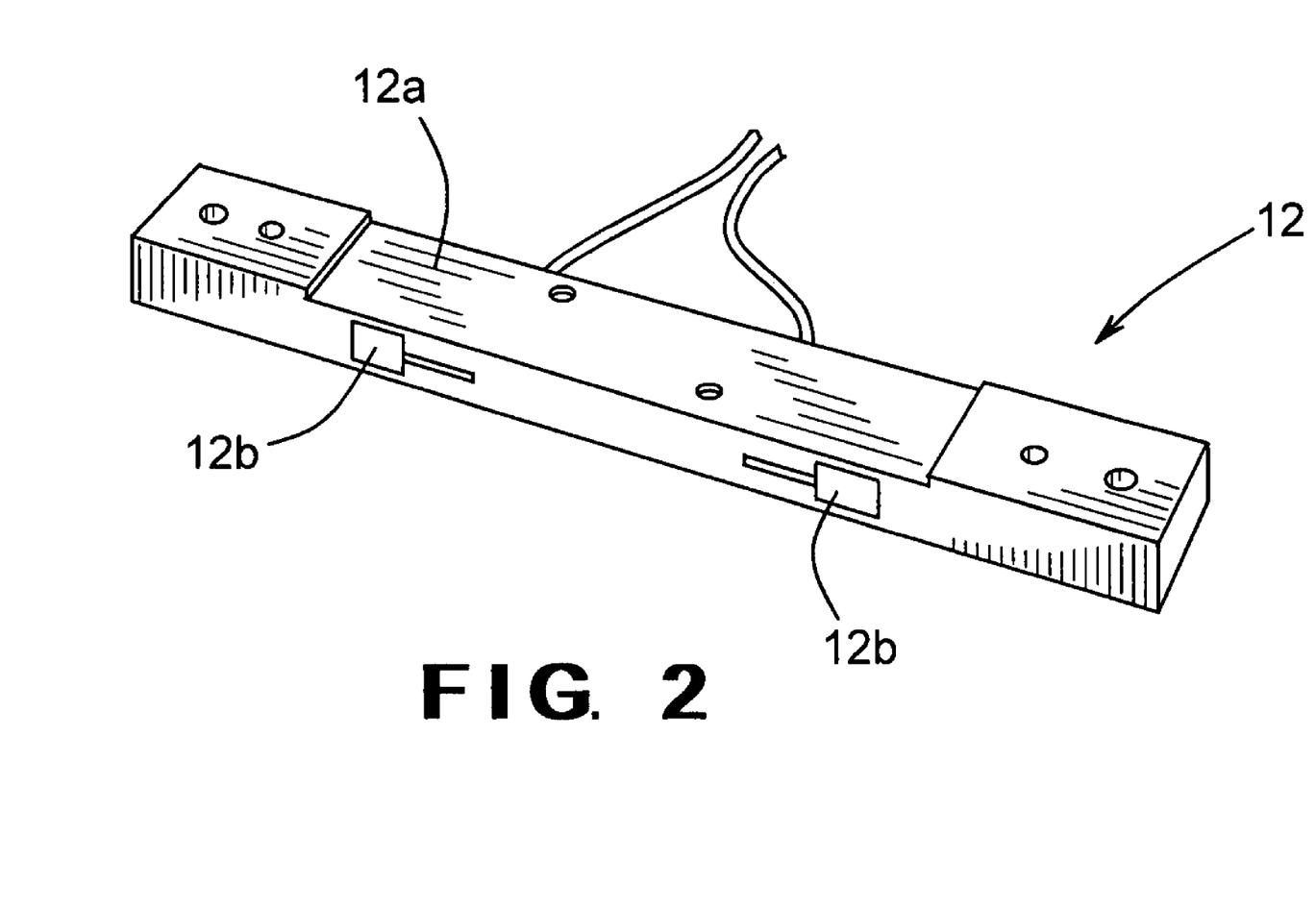
FIG. 2 is a perspective view of a load cell assembly that can be used in the testing apparatus illustrated in FIG. 1 for measuring the amount of force that is applied during the crimping operation.

Referring now to the drawings, there is illustrated in FIG. 1 a portion of an apparatus, indicated generally at 10, for testing the quality of crimped seals that will be formed in overlapping portions of a sheet of the packaging material, such as by a conventional form, fill, and seal apparatus (not shown) described above. The testing apparatus 10 includes a base 11 having a load cell assembly, such as a dual beam load cell assembly indicated generally at 12, secured thereto. The structure of the load cell assembly 12 is illustrated in detail in FIG. 2. As shown therein, the load cell assembly 12 includes a housing 12a that encloses a pair of force transducers 12b. The housing 12a is preferably formed from a relatively strong, rigid material, such as steel or a similar metallic material. The force transducers 12b are conventional in the art and are each adapted to generate electrical signals that are representative of the amount of compressive force that is exerted thereon. The purpose for the load cell assembly 12 will be explained below.

A lower crimper 13 is mounted on the load cell assembly 12 so as to be supported on the base 11 of the testing apparatus 10. The lower crimper 13 is conventional in the art and may be embodied as any desired structure that is adapted to engage and form seals in overlapping portions of the sheet of the packaging material. A variety of structures for the lower crimper 13 are described and illustrated in the above-referenced patents. However, it will be appreciated that this invention may be practiced using any desired structure for the lower crimper 13.

A ram assembly, indicated generally at 14, is also secured to the base 11 of the testing apparatus 10. The ram assembly 14 is conventional in the art and supports an upper crimper 15 thereon for vertical movement relative to the lower crimper 13. The upper crimper 15 is vertically movable between a retracted position (illustrated in FIGS. 1, 5, 6, and 7), wherein the upper crimper 15 is spaced apart from the lower crimper 13, and an extended position (illustrated in FIG. 8), wherein the upper crimper is moved into engagement with the lower crimper 13. The upper crimper 15 is conventional in the art and may be embodied as any desired structure that is adapted to engage and form seals in overlapping portions of the sheet of the packaging material. A variety of structures for the upper crimper 15 are described and illustrated in the above-referenced patents. However, it will be appreciated that this invention may be practiced using any desired structure for the upper crimper 15. The purpose for the ram assembly 14 will also be described below.

Figure 3:
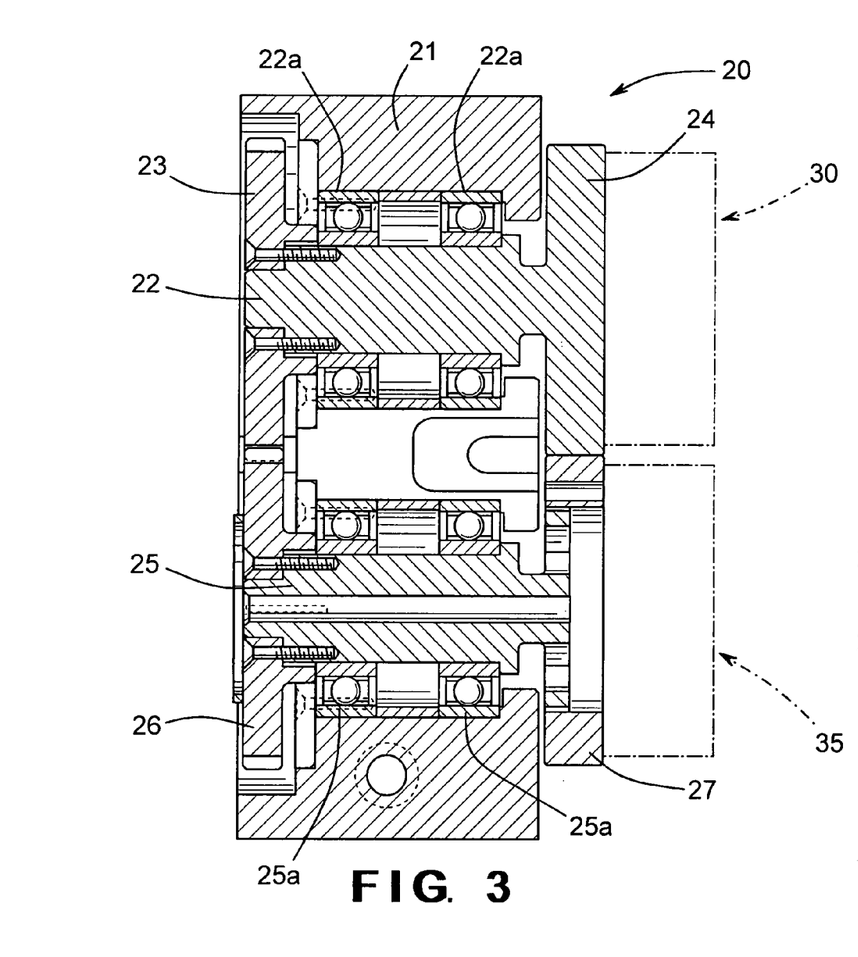
FIG. 3 is a sectional elevational view of a block assembly portion of the testing apparatus illustrated in FIGS. 1 and 2.
Figure 4:
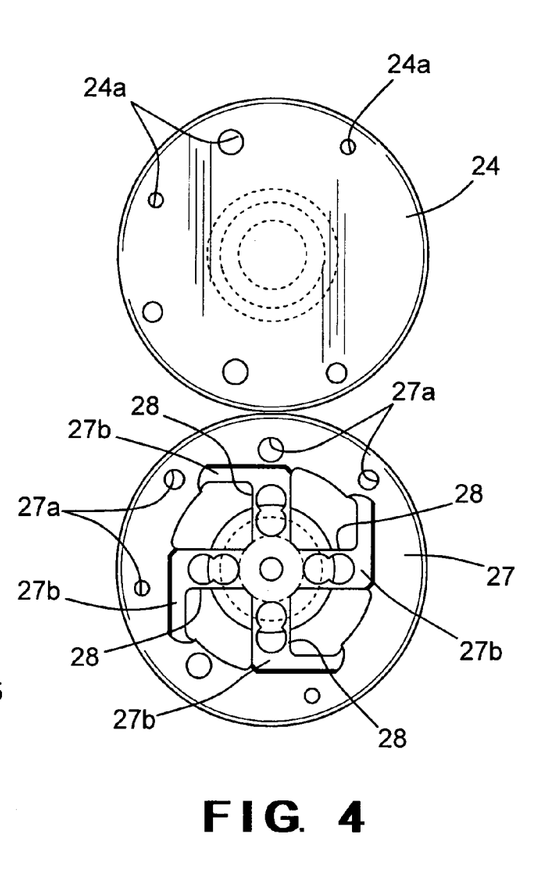
FIG. 4 is an end elevational view of a portion of the block assembly illustrated in FIG. 3 showing a torque measuring transducer.

The testing apparatus further includes a block assembly, indicated generally at 20, for supporting, manipulating, and testing a test strip of a packaging material for use with the lower and upper crimpers 13 and 15 described above. As best shown in FIG. 3, the block assembly 20 includes a housing 21 that supports an upper driveshaft 22 for rotation relative thereto. To accomplish this, the upper driveshaft 22 is supported by a pair of roller bearings 22a that are press fit in or otherwise supported on the housing 21. The upper driveshaft 22 has an upper drive gear 23 that is provided at one end thereof. In the illustrated embodiment, the upper drive gear 23 is formed as a separate piece that is secured to the upper driveshaft 22, although such is not necessary. The upper driveshaft 22 further has an upper clamp support 24 that is provided at the other end thereof. In the illustrated embodiment, the upper clamp support 24 is formed integrally with the upper driveshaft 22, although such is not necessary. The upper clamp support 24 is generally cylindrical in shape, including an upper clamp mounting region that is defined by a plurality of mounting apertures 24a formed about the periphery of an outwardly facing surface thereof. The purpose for such mounting apertures 24a will be explained below. As shown in FIGS. 3 and 4, the portion of the upper clamp support 24 that extends radially outwardly from the upper driveshaft 22 to the upper clamp mounting region where the mounting apertures 24a are provided is generally solid. Thus, the upper clamp mounting region is fixed in position relative to the upper driveshaft 22.

Similarly, the housing 21 of the block assembly 20 supports a lower driveshaft 25 for rotation relative thereto. To accomplish this, the lower driveshaft 25 is supported by a pair of roller bearings 25a that are press fit in or otherwise supported on the housing 21. The lower driveshaft 25 has a lower drive gear 26 that is provided at one end thereof. In the illustrated embodiment, the lower drive gear 26 is formed as a separate piece that is secured to the lower driveshaft 25, although such is not necessary. The lower driveshaft 25 further has a lower clamp support 27 that is provided at the other end thereof. In the illustrated embodiment, the lower clamp support 27 is formed integrally with the lower driveshaft 25, although such is not necessary. The lower clamp support 27 is generally cylindrical in shape, including a lower clamp mounting region that is defined by a plurality of mounting apertures 27a formed about the periphery of an outwardly facing surface thereof. The purpose for such mounting apertures 27a will be explained below. As shown in FIGS. 3 and 4, the portion of the lower clamp support 27 that extends radially outwardly from the lower driveshaft 25 to the lower clamp mounting region where the mounting apertures 27a are provided is not solid, as described above. Rather, portions of the lower clamp support 27 have been removed to provide a plurality of spoke-like arms 27b that extend radially outwardly from the lower driveshaft 25 to the lower clamp mounting region 27 wherein the mounting apertures 27a are provided. Thus, the lower clamp mounting region is relatively flexible relative to the lower driveshaft 25. A plurality of strain gauges 28 or other force measuring structures are provided on the arms 27b of the lower clamp support 27 for a purpose that will be described below.

As shown in FIG. 3, it can be seen that the upper drive gear 23 and the lower drive gear 26 mesh with one another. As a result, the upper driveshaft 22 and the lower driveshaft 25 are connected together for concurrent rotation, albeit in opposite rotational directions. A conventional drive system (not shown) cooperates with either the upper drive gear 23 or the lower drive gear 26 (or, for that matter, any other portion of the upper driveshaft 22 and the lower driveshaft 25) to selective effect rotation thereof in the manner described below. Preferably, however, the drive system cooperates with the upper drive gear 23 to keep any load generated by the drive system off of the lower driveshaft 25 and, therefore, from affecting the strain gauges 28.

Figure 5:
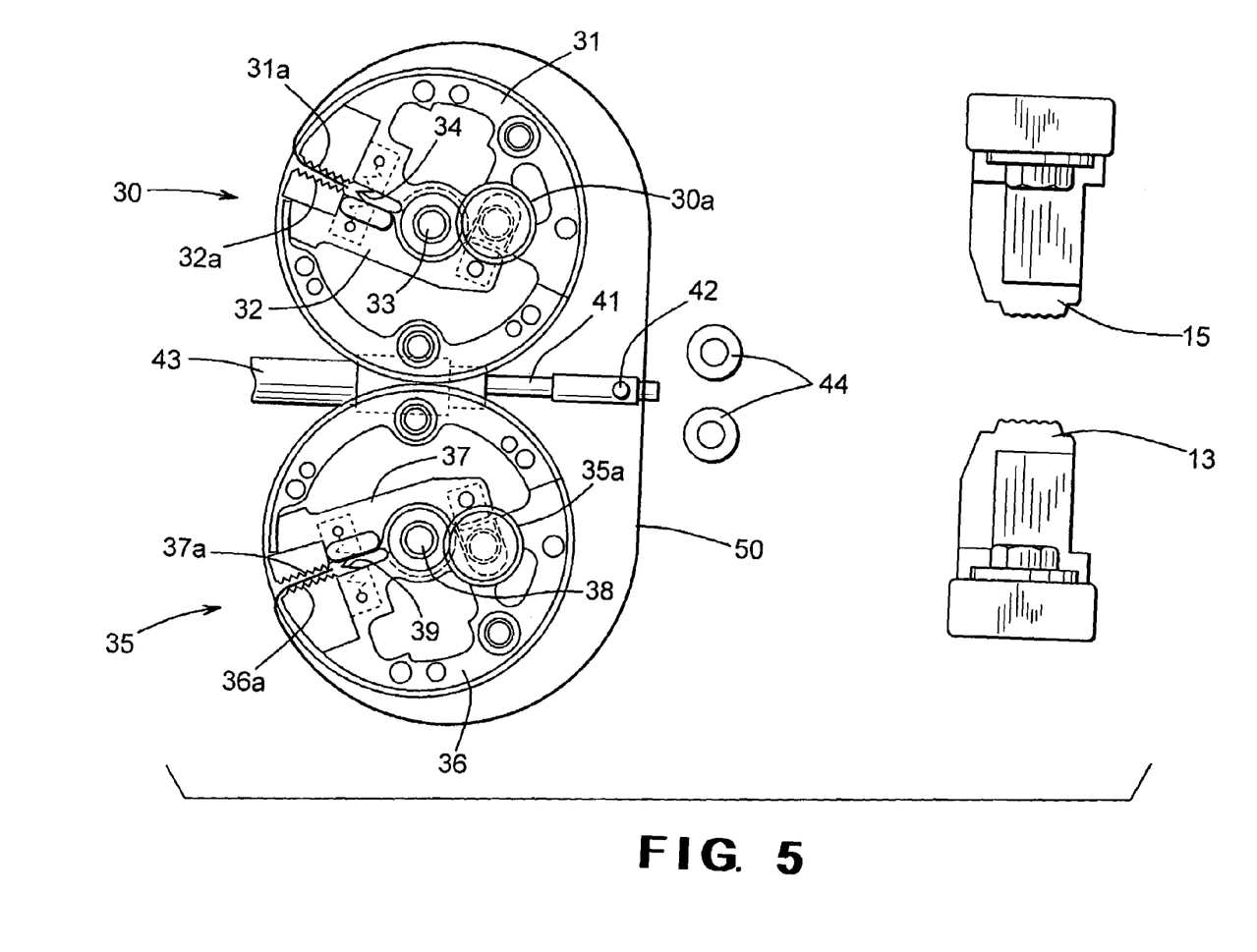
FIG. 5 is an end elevational view of a portion of the testing apparatus illustrated in FIGS. 1 and 2 showing the components in an initial loading position.

An upper clamp, indicated generally at 30, is secured to the upper clamp support 24 by a plurality of threaded fasteners (not shown) that extend therethrough into cooperate with respective ones of the plurality of mounting apertures 24a. The structure of the upper clamp 30 is best illustrated in FIG. 5. As shown therein, the upper clamp 30 includes a first clamp member 31 and a second clamp member 32. The illustrated clamp members 31 and 32 are generally clamshell-shaped, although such is not required. The clamp members 31 and 32 have respective serrated gripping surfaces 31a and 32a provided thereon. The first clamp member 31 is supported for pivoting movement relative to the second clamp member 32 by a pivot pin 33. The second clamp member 32 is pivotable relative to the first clamp member 31 between an opened position (illustrated in FIG. 5), wherein the gripping surfaces 31a and 32a are spaced apart from one another, and a closed position (illustrated in FIG. 6), wherein the gripping surfaces 31a and 32a are disposed adjacent and engage one another. A spring 34 is provided to resiliently urge the first and second clamp members 31 and 32 toward the closed position. The purpose for the upper clamp 30 will be explained below.

A lower clamp, indicated generally at 35, is secured to the lower clamp support 27 by a plurality of threaded fasteners (not shown) that extend therethrough into cooperate with respective ones of the plurality of mounting apertures 27a. The structure of the lower clamp 35 is best illustrated in FIG. 5. As shown therein, the lower clamp 35 includes a first clamp member 36 and a second clamp member 37. The illustrated clamp members 36 and 37 are generally clamshell-shaped, although such is not required. The clamp members 36 and 37 have respective serrated gripping surfaces 36a and 37a provided thereon. The first clamp member 36 is supported for pivoting movement relative to the second clamp member 37 by a pivot pin 38. The second clamp member 37 is pivotable relative to the first clamp member 36 between an opened position (illustrated in FIG. 5), wherein the gripping surfaces 36a and 37a are spaced apart from one another, and a closed position (illustrated in FIG. 6), wherein the gripping surfaces 36a and 37a engage one another. A spring 39 is provided to resiliently urge the first and second clamp members 36 and 37 toward the closed position. The purpose for the lower clamp 35 will be explained below.

If desired, a pair of locking structures can be provided for positively retaining the second clamp members 32 and 37, respectively, in their closed positions relative to the first clamp members 31 and 36, respectively. For example, the upper clamp 30 can include a knurled thumb screw 30a having a threaded shank portion that is threaded into a correspondingly threaded aperture formed in the upper clamp 30. The end of the threaded shank portion is conical in shape and is aligned with a gap (not shown) defined between portions of the first clamp member 31 and the second clamp member 32 located on the opposite side of the pivot pin 33 from the serrated gripping surfaces 31a and 32a. When the knurled thumb screw 30a is tightened, the conical tip of the threaded shank portion is extended into that gap so as to move the portions of the first and second clamp members 31 and 32 apart from one another. Consequently, the serrated gripping surfaces 31a and 32a of the first and second clamp members 31 and 32 are positively moved together. Similarly, the lower clamp 35 can include a knurled thumb screw 35a that functions in the same manner to positively move the second clamp member 37 to its closed position relative to the first clamp member 36.

Referring back to FIG. 1, it can be seen that the testing apparatus 10 further includes an extension arm assembly, indicated generally at 40, that is supported on the block assembly 20 for movement relative thereto. The extension arm assembly 40 is located adjacent to the upper and lower clamps 30 and 35 and includes a laterally extending extension arm 41 having a transversely extending pick-up arm 42 provided at or near a first end thereof. The second end of the extension arm 41 is connected to an actuator 43 that is supported on the block assembly 20. In the illustrated embodiment, the actuator 43 is a pneumatic cylinder, and the second end of the extension arm 41 extends within the pneumatic cylinder 43 and functions as a piston. By supplying pressurized air to the pneumatic cylinder 43 in a conventional manner, the extension arm 41 and the pick-up arm 42 can be selectively moved laterally relative to the block assembly 20 between a retracted position (illustrated in FIG. 5), wherein the pick-up arm 42 is located adjacent to the upper and lower clamps 30 and 35, and an extended position (illustrated in FIG. 7), wherein the pick-up arm 42 is located adjacent to the upper and lower crimpers 13 and 15. The extension arm assembly 40 further includes a pair of guide rollers 44 that can also be supported on the block assembly 20. The purposes for the various components of the extension arm assembly 40 will be explained below.

The operation of the testing apparatus 10 will now be described with reference to FIG. 5 through 10. FIG. 5 illustrates the various components of the testing apparatus 10 in an initial loading position, wherein a test strip 50 of the packaging material can be installed therein. To accomplish this, the extension arm assembly 40 is initially positioned in the retracted position such that the pick-up arm 42 is located adjacent to the upper and lower clamps 30 and 35. To install a first end of the test strip 50 of the packaging material, the clamp members 31 and 32 of the upper clamp 30 are manually moved by an operator of the testing apparatus 10 to the opened position against the urging of the spring 34. As mentioned above, this causes the respective gripping surfaces 31a and 32a to be spaced apart from one another. The first end of a test strip 50 of the packaging material is then inserted between the two gripping surfaces 31a and 32a until the end thereof abuts a positive stop (not shown) provided therein. Thereafter, the operator releases the clamp members 31 and 32, and the gripping surfaces 31a and 32a are moved to the closed position under the urging of the spring 34. As a result, the first end of the test strip 50 of the packaging material is frictionally engaged by the gripping surfaces 31a and 32a of the upper clamp 30. If desired, the knurled thumb screw 30a can then be tightened to positively retain the second clamp member 32 in its closed position relative to the first clamp member 31. The other end of the test strip 50 of the packaging material is wrapped about a portion of the outer surface of the upper clamp 30, downwardly between the transversely extending pick-up arm 42 on the one hand and the guide rollers 44 on the other hand, and about a portion of the outer surface of the lower clamp 35. Similarly, to install a second end of the test strip 50 of the packaging material, the clamp members 36 and 37 of the lower clamp 35 are manually moved by an operator of the testing apparatus 10 to the opened position against the urging of the spring 39. As mentioned above, this causes the respective gripping surfaces 36a and 37a to be spaced apart from one another. The second end of the test strip 50 of the packaging material is then inserted between the two gripping surfaces 36a and 37a until the end thereof abuts a positive stop (not shown) provided therein. Thereafter, the operator releases the clamp members 36 and 37, and the gripping surfaces 36a and 37a are moved to the closed position under the urging of the spring 39. As a result, the second end of the test strip 50 of the packaging material is frictionally engaged by the gripping surfaces 36a and 37a of the lower clamp 35. Again, if desired, the knurled thumb screw 35a can then be tightened to positively retain the second clamp member 37 in its closed position relative to the first clamp member 36.

Figure 6:
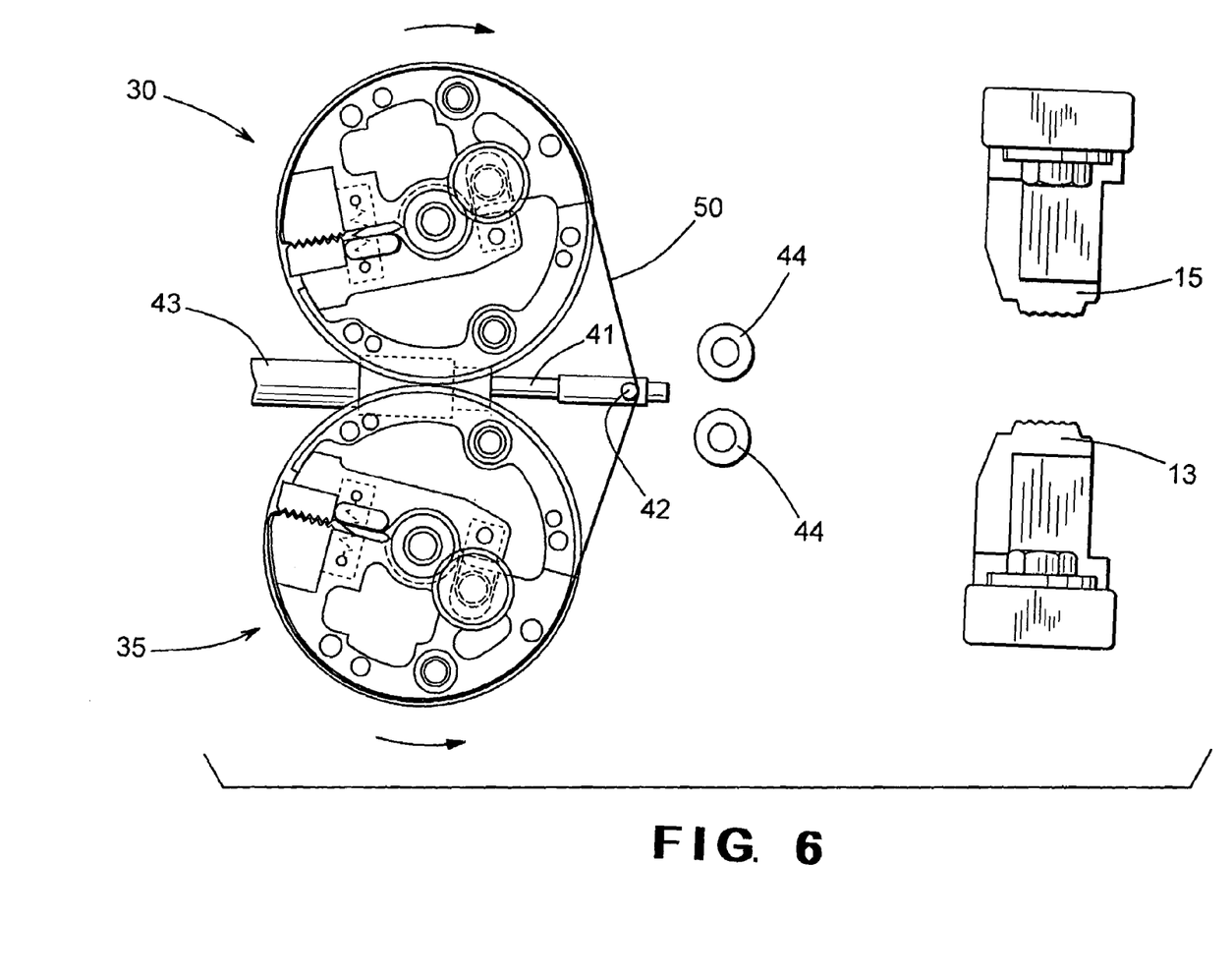
FIG. 6 is an end elevational view similar to FIG. 5 showing the components in a tensioned position.
Figure 7:
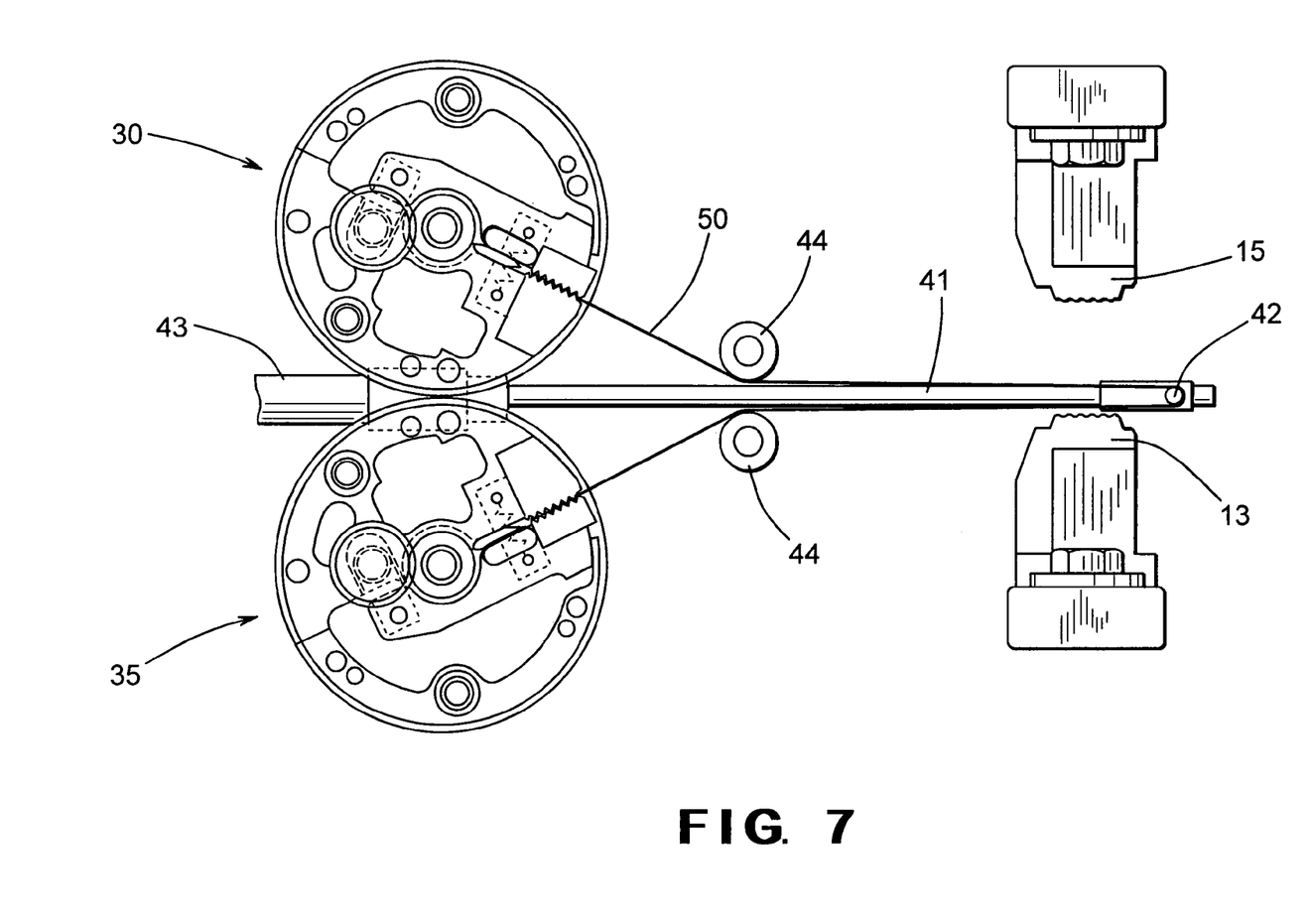
FIG. 7 is an end elevational view similar to FIG. 5 showing the components in an extended position.

Next, as shown in FIGS. 6 and 7, the testing apparatus 10 is operated to extend a portion of the test strip 50 of the packaging material laterally from the block assembly 20 to between the lower crimper 13 and the upper crimper 15. To accomplish this, the pneumatic cylinder 43 is actuated to extend the extension arm 41 and the pick-up arm 42 laterally from the retracted position to the extended position. As shown in FIG. 6, such lateral movement causes the pick-up arm 42 to engage a portion of the test strip 50 of the packaging material that is located intermediate of the upper and lower clamps 30 and 35 and push such intermediate portion of the test strip 50 toward the upper and lower crimpers 13 and 15. During this extension of the test strip 50 of the packaging material, the upper and lower driveshafts 22 and 25 (and the upper and lower clamps 30 and 35 mounted thereon) of the block assembly 20 rotate in the direction of the arrows indicated in FIG. 6. Thus, little resistance is offered as extension arm assembly 40 pushes the intermediate portion of the test strip 50 of the packaging material from the upper and lower clamps 30 and 35. As shown in FIG. 7, further lateral movement of the extension arm assembly 40 causes the intermediate portion of the test strip 50 of the packaging material to be pushed laterally between the two guide rollers 44 and between the upper and lower crimpers 13 and 15 (which are located in the retracted position described above). Throughout the entire extension of the test strip 50 of the packaging material, the ends of such test strip 50 remain frictionally engaged by the respective upper and lower clamps 30 and 35.

Figure 8:
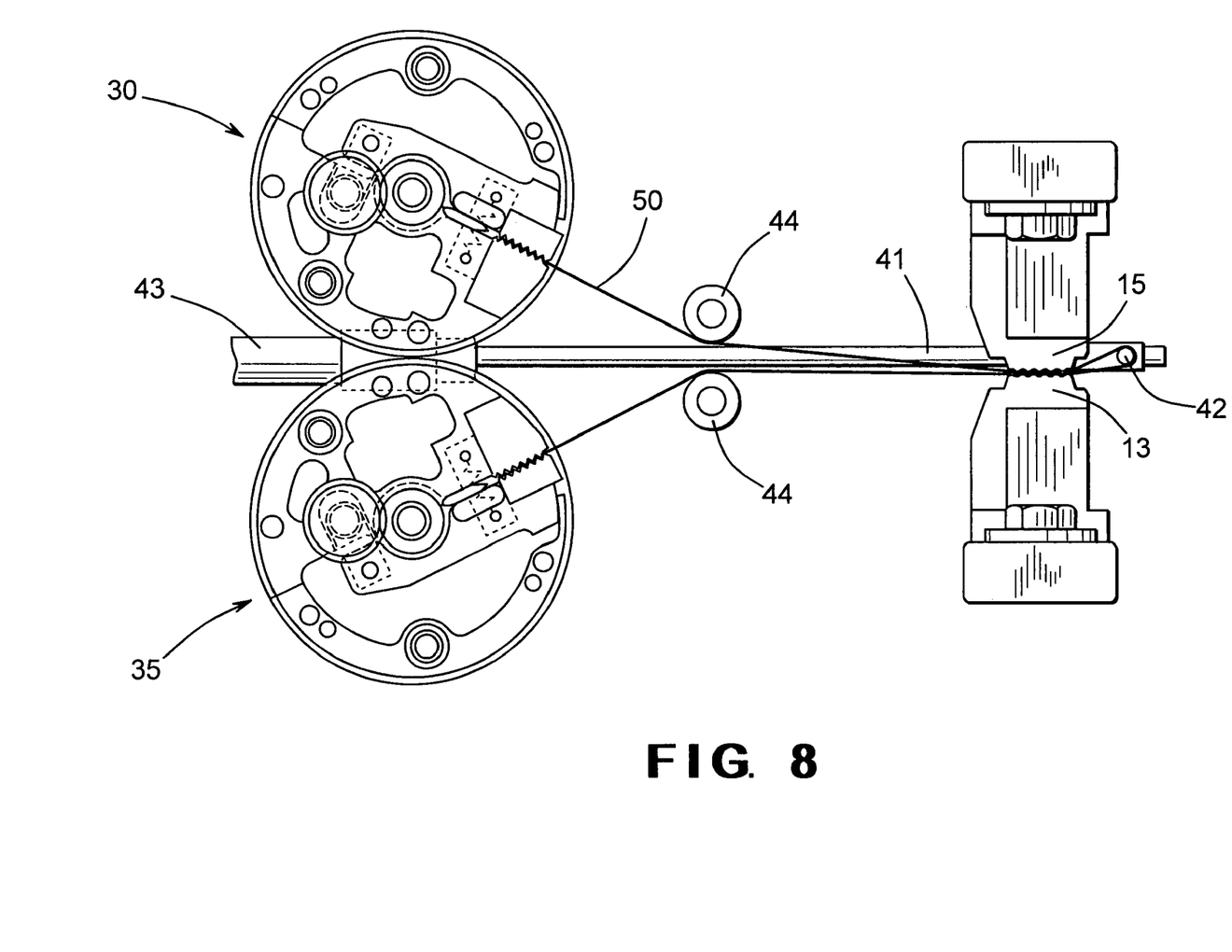
FIG. 8 is an end elevational view similar to FIG. 5 showing the components in a sealing position.

Next, as shown in FIG. 8, the ram assembly 14 of the testing apparatus 10 is actuated to move the upper crimper 15 vertically downwardly from the retracted position to the extended position, wherein a portion 50a (see FIG. 9) of the test strip 50 of the packaging material is compressed and sealed between the lower crimper 13 and the upper crimper 15. This operation of the testing apparatus 10 is preferably intended to simulate the conditions under which the packaging material used to form the test strip 50 will be compressed and sealed under normal production operation of the form, fill, and seal apparatus. Thus, the various operating conditions (such as magnitude of pressure, time duration, and temperature, for example) under which the lower and upper crimpers 13 and 15 compress and seal the portion 50a of the test strip 50 of the packaging material are preferably selected to simulate the same operating conditions that would be encountered during normal production operation.

The load cell assembly 12 can be used to measure the magnitude of the pressure that is exerted by the lower and upper crimpers 13 and 15 on the test strip 50 as the packaging material. As mentioned above, the force transducers 12b contained within the load cell assembly 12 are each adapted to generate electrical signals that are representative of the amount of compressive force that is exerted thereon. Thus, when the upper crimper 15 compresses and seals the portion 50a of the test strip 50 of the packaging material against the lower crimper 13, the force transducers 12b can generate electrical signals that are representative of the amount of force that is exerted thereon. Although this function can be accomplished by providing a single force transducer 12b in a single load cell assembly, it has been found preferable to provide two of such force sensors 12b in a dual beam load cell assembly 12. This is because it has been found that the amount of force that is exerted by the upper crimper 15 against the lower crimper 13 may not always be applied uniformly across the length thereof. When this occurs, the amount of force that is exerted by the upper crimper 15 against one end of the lower crimper 13 may be significantly different from the amount of force that is exerted by the upper crimper 15 against the other end of the lower crimper 13. A single force transducer 12b would not detect this condition, but rather would generate a single electrical signal that is representative of a somewhat average magnitude of force, i.e., a magnitude of force that is somewhat greater than the smaller amount of force that is exerted on one end of the crimpers 13 and 15, but is somewhat less than the larger amount of force that is exerted on the other end of the lower crimpers 13 and 15. By providing a pair of force transducers 12b that are spaced apart from one another, this condition of unequal force distribution can be easily detected and corrected by adjusting the testing apparatus 10.

Figure 9:
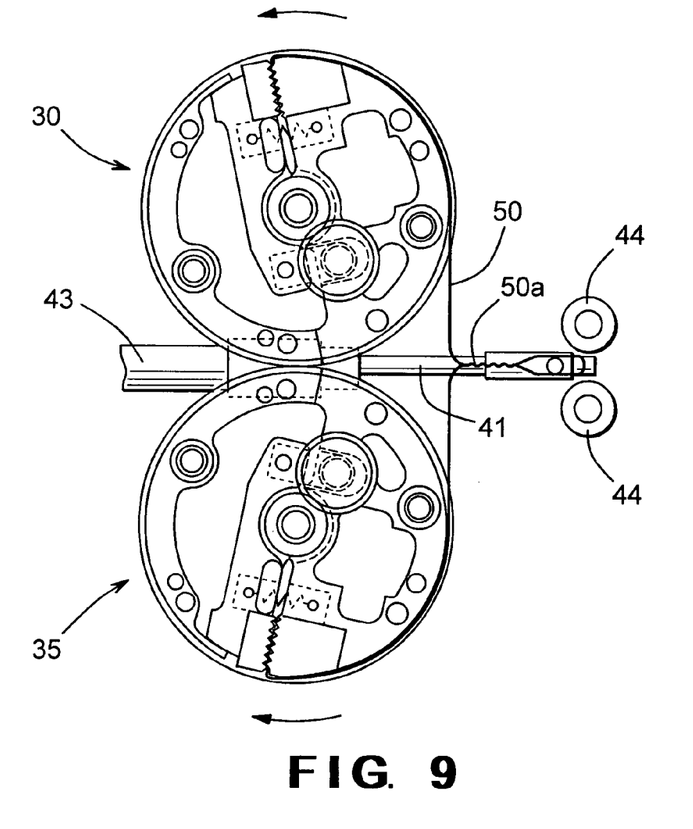
FIG. 9 is an end elevational view similar to FIG. 5 showing the components in a seal strength testing position.

Once the sealing process has been completed, the upper crimper 15 is moved back to the retracted position, thereby releasing the sealed portion 50a of the test strip 50 of the packaging material. Then, the block assembly 20 is actuated to rotate the clamps 30 and 35 in the direction of the arrows indicated in FIGS. 9 and 10. As a result, the ends of the test strip 50 of the packaging material are re-wound upon the clamps 30 and 35. As this occurs, the extension arm assembly 40 is moved toward the retracted position, as shown in FIG. 9, so that the extension arm assembly 40 provides no mechanical resistance to the re-winding of the ends of the test strip 50 of the packaging material are re-wound upon the clamps 30 and 35. Accordingly, this initial re-winding of the ends of the test strip 50 can occur rapidly.

This rapid initial re-winding of the ends of the test strip 50 of the packaging material continues until the sealed portion 50a of the test strip 50 is pulled taut by the clamps 30 and 35 (or, more preferably, just before the sealed portion 50a of the test strip 50 is pulled taut by the clamps 30 and 35). Thereafter, the clamps 30 and 35 are continued to be rotated in the same direction as indicated by the arrows so as to pull the sealed portion 50a of the test strip 50 of the packaging material apart. Preferably, such further rotation occurs at a slower speed than the initial rapid re-winding of the ends of the test strip 50, although such is not necessary. Regardless, the continued rotation of the clamps 30 and 35 causes the sealed portions of the test strip 50 of the packaging material to be separated from one another. As this separation occurs, the amount of force that is being applied by the clamps 30 and 35 to the ends of the test strip 50 of the packaging material can be measured by the strain gauges 28 that are provided on the arms 27b of the lower clamp support 27. As mentioned above, these spoke-like arms 27b extend radially outwardly from the lower driveshaft 25 to the lower clamp mounting region 27 wherein the mounting apertures 27a are provided. Thus, the lower clamp mounting region (which is where the lower clamp 35 is secured) is relatively flexible relative to the lower driveshaft 25. Consequently, when force is exerted by the lower clamp 35 to cause the sealed portions of the test strip 50 of the packaging material to be separated from one another, the spoke-like arms 27b will flex somewhat. Such flexure can be measured by the strain gauges 28 so as to generate electrical signals that are representative of the amount of force that is being exerted.

Figure 10:
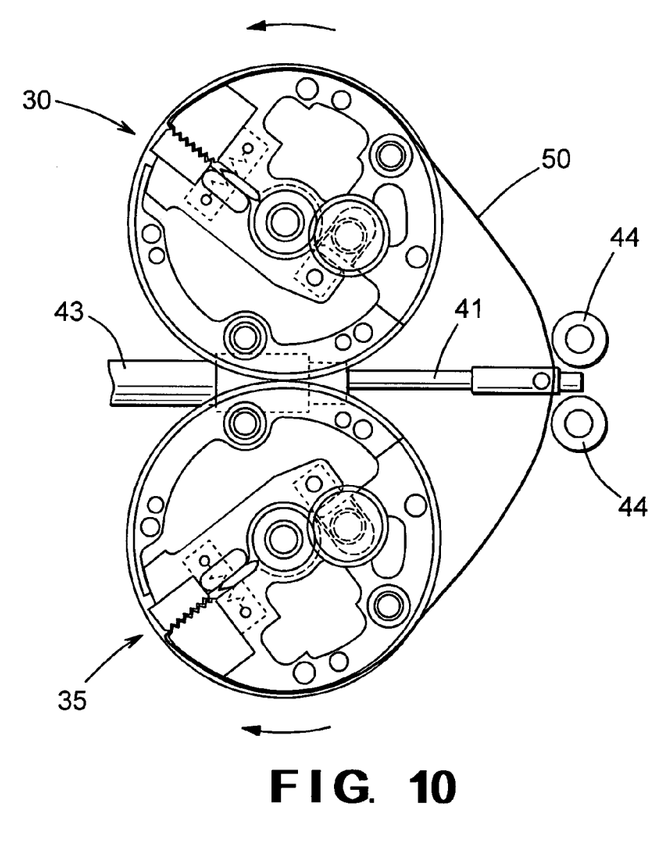
FIG. 10 is an end elevational view similar to FIG. 5 showing the components after the completion of the test.

After a period of such separation, the sealed portion 50a of the test strip 50 of the packaging material will become completely separated, as shown in FIG. 10. When this occurs, the amount of force that is being exerted by the lower clamp 35 will decrease rather abruptly. At that point, the testing process has been completed. Thereafter, the clamp members 31 and 32 of the upper clamp 30 can be manually moved by an operator of the testing apparatus 10 to the opened position against the urging of the spring 34 to release the first end of the test strip 50, and the clamp members 36 and 37 of the lower clamp 35 can be manually moved by an operator of the testing apparatus 10 to the opened position against the urging of the spring 39 to release the second end of the test strip 50.

The operation of the testing apparatus 10 described above can be controlled by a conventional microprocessor (not shown) or similar programmable controller in a manner that is well known in the art. The microprocessor can also be programmed to measure the various parameters of the testing process, including the various operating conditions (such as magnitude of pressure, time duration, and temperature, for example) under which the lower and upper crimpers 13 and 15 compress and seal the portion 50a of the test strip 50 of the packaging material, the amount of force that is exerted to separate the sealed portion 50a of the test strip 50, and the amount of time that is required to complete the testing process. Some or all of such parameters may be stored in the microprocessor and displayed on a visual display for convenience.

In accordance with the provisions of the patent statutes, the principle and mode of operation of this invention have been explained and illustrated in its preferred embodiment. However, it must be understood that this invention may be practiced otherwise than as specifically explained and illustrated without departing from its spirit or scope.

What is claimed is:

1. A method comprising the steps of:
    (a) installing first and second ends of a packaging material respectively on first and second clamps;
    (b) while the first and second ends of the packaging material are installed respectively on the first and second clamps, extending a portion of the packaging material intermediate the first and second ends between first and second crimpers;
    (c) moving the first and second crimpers into engagement with the extended intermediate portion of the packaging material to form a crimped seal;
    (d) moving the first and second crimpers out of engagement with the intermediate portion of the packaging material; and
    (e) moving the first and second clamps to pull apart the crimped seal.

2. The method defined in claim 1 wherein said step (a) is performed by installing the first and second ends of a packaging material respectively on the first and second clamps such that the intermediate portion of the packaging material is disposed adjacent to an extension arm assembly, and wherein said step (b) is performed by operating the extension arm assembly to extend the intermediate portion of the packaging material between the first and second crimpers.

3. The method defined in claim 1 wherein said step (b) is performed by extending the intermediate portion of the packaging material between first and second guide rollers and between the first and second crimpers.

4. The method defined in claim 1 wherein said step (c) includes the additional step of measuring an amount of force exerted by the first and second crimpers on the intermediate portion of the packaging material.

5. The method defined in claim 1 wherein said step (d) is performed by rotating the first and second clamps.

6. The method defined in claim 5 wherein said step (d) is performed by rotating the first and second clamps in opposite rotational directions.

7. The method defined in claim 1 including a further step (f) of measuring an amount of force exerted by the first and second clamps to pull apart the crimped seal while step (e) is being performed.

8. An apparatus comprising:
    a base;
    first and second clamps provided on the base for selectively supporting first and second ends of a packaging material;
    first and second crimpers provided on the base;
    a extension arm assembly provided on the base for selectively extending an portion of the packaging material intermediate the first and second ends between first and second crimpers;
    a mechanism provided on the base for selectively moving the first and second crimpers between a retracted position, wherein the first and second crimpers are spaced apart from one another, and an extended position, wherein the first and second crimpers engage the intermediate portion of the packaging material disposed therebetween to form a crimped seal; and
    a mechanism provided on the base for selectively moving the first and second clamps to pull apart the crimped seal.

9. The apparatus defined in claim 8 further including a sensor for measuring an amount of force exerted by the first and second crimpers on the intermediate portion of the packaging material.

10. The apparatus defined in claim 8 wherein said mechanism selectively rotates the first and second clamps to pull apart the crimped seal.

11. The apparatus defined in claim 10 wherein said mechanism selectively rotates the first and second clamps in opposite rotational directions to pull apart the crimped seal.

12. The apparatus defined in claim 8 further including a sensor for measuring an amount of force exerted by the first and second clamps to pull apart the crimped seal.

* * * * *